United States Patent
Hohn-Stöcker et al.

(10) Patent No.: US 6,172,035 B1
(45) Date of Patent: Jan. 9, 2001

(54) PREPARATION OF THICKENING AGENTS BASED ON FATTY ACID MONOISOPROPANOLAMIDE, USE THEREOF AND PREPARATIONS CONTAINING SAME

(75) Inventors: Elke Hohn-Stöcker, Schlüchtern; Christl Möller, Steinau an der Strasse, both of (DE); Patrice Bayle, Marcel (FR)

(73) Assignee: Goldschmidt Rewo GmbH & Co. KG (DE)

( * ) Notice: Under 35 U.S.C. 154(b), the term of this patent shall be extended for 0 days.

(21) Appl. No.: 09/510,204

(22) Filed: Feb. 22, 2000

(30) Foreign Application Priority Data

Mar. 2, 1999 (DE) .............................................. 199 08 944

(51) Int. Cl.$^7$ .................................. C11D 3/20; C11D 3/32
(52) U.S. Cl. .......................... 510/501; 510/119; 510/126; 510/130; 510/137; 510/158; 510/159; 510/506; 564/123; 564/215

(58) Field of Search ..................................... 510/119, 126, 510/130, 137, 158, 159, 501, 506; 564/123, 215

(56) References Cited

U.S. PATENT DOCUMENTS 3,856,711  12/1974  Mausner et al. ..................... 510/413

FOREIGN PATENT DOCUMENTS 693 14 698
T2  12/1993  (DE) .

*Primary Examiner*—Gregory R. Delcotto
(74) *Attorney, Agent, or Firm*—Scully, Scott, Murphy & Presser

(57) ABSTRACT

Thickening agents based on fatty acid monoisopropanolamide which are etherified with ethylene oxide and/or propylene oxide, their use in surface-active formulations and formulations comprising an active amount of these thickening agents.

11 Claims, No Drawings

PREPARATION OF THICKENING AGENTS BASED ON FATTY ACID MONOISOPROPANOLAMIDE, USE THEREOF AND PREPARATIONS CONTAINING SAME

FIELD OF THE INVENTION

The present invention relates to thickening agents based on fatty acid monoisopropanolamide which are etherified with ethylene oxide and/or propylene oxide, their use in surface-active formulations and formulations comprising an active amount of these thickening agents.

BACKGROUND OF THE INVENTION

Liquid detergent mixtures for domestic and industrial use such as dishwashing agents, laundry detergents, cleaners, cleaning gels for the sanitary sector and; for cosmetic products such as hair shampoos, shower gels and liquid soaps frequently do not have the desired viscous consistency. The viscous consistency of prior art liquid detergent mixtures is, in any event, disadvantageous from an application aspect, but in particular in relation to products for personal use in skin cleaning, skin care and cosmetics is criticized as unfavorable.

When the viscosity is too low, economical dosage is not exactly simple; the contact and the residence/exposure time on the respective surfaces are too short and, when used by hand in the personal sector, the products tend to drain away between one's fingers.

A multiplicity of thickening agents have therefore been proposed in the prior art for surface-active preparations. For example, U.S. Pat. No. 3,856,711 discloses fatty acid amides based on dialkanolamines such as diethanolamine. However, these thickening agents are no longer acceptable because of the potential nitrosamine formation and the associated carcinogenic potential. It is true that thickening agents based on fatty acids and monoisopropanolamine do not have this disadvantage, but their thickening action only develops at elevated amide concentrations, and such thickening agents attain maximum/optimum thickening action only in the presence of sufficiently large amounts of mineral salts. Large amounts of mineral salts are undesirable from an application viewpoint since high concentrations of mineral salts can cause corrosion problems in storage and produce formulations which are less stable at low temperatures. Typically, the monoisopropanolamides of the fatty acids generally used are pasty or solid, and this is likewise an obstacle in application since the monoisopropanolamides are more energy-intensive to incorporate into formulations.

EP-B-0 574 277 proposes the use of the monoisopropanolamide of isostearic acid as a thickening agent. This disclosure provides an improvement in the thickening properties even at low levels and at reduced mineral salt concentrations. Moreover, the product is liquid and relatively easy to process at room temperature (RT).

This represents a significant advance from an application viewpoint, but these compounds are still in need of improvement with regard to their stability in storage, especially at low temperatures.

This is because it has been determined that, in the course of storage, solid fractions settle out from the initially clear product and form a solid sediment. Before use, the thickening agents of EP-B-0 574 277 have to first be remelted and rehomogenized by intensive stirring. The individual use of both of the decanted clear fraction and the solid fraction is not as effective as if the two are used together.

In addition, this procedure results in an undesirable yield loss and/or additional technical complications for the formulator. Moreover, it is impossible to be confident that the end formulation will not develop storage and/or other problems.

It is accordingly an object of the present invention to avoid these problems of the prior art product and to improve its stability in storage, not only at room temperature, but also at low temperatures.

SUMMARY OF THE INVENTION

This object is achieved, surprisingly, by reacting the monoisopropanolamide of isostearic acid and the monoisopropanolamide of canola fatty acid with propylene oxide and/or ethylene oxide.

The present invention thus provides compounds of the general formula (I)

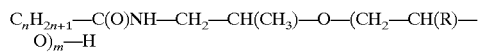

where n is from 13 to 17, especially an isostearoyl radical or a canola fatty acid radical; R is H or $CH_3$; and m is from 1.5 to 5.5, especially 2.5 to 4.0.

DETAILED DESCRIPTION OF THE INVENTION

The amide formation of the first step can take place according to known methods of preparing amides. Preference is given to using the process described in EP-B-0 574 277, wherein a stoichiometric amount or a slight excess (about 1.1 mol) of isopropanolamine (also known as 1-amino-2-propanol, 2-hydroxypropylamine, monoisopropanolamine or, for short, MIPA) is added to isostearic acid, which has been preheated to 40–70° C. and pretreated with an antioxidant, or to canola fatty acid and the temperature is allowed to rise to 90 to 110° C. Thereafter, 2–5 parts by weight of phosphoric acid are added as a catalyst per 10,000 parts by weight of isostearic acid or canola fatty acid and the temperature is raised to 145–170° C. As soon as the acid number of the mixture is less than 5 (mg KOH/g), a second amount of antioxidant is added and the reaction is completed at a reduced pressure of $4–1.9 \times 10^3$ Pa and thereafter the excess of MIPA is removed.

The subsequent ethoxylation and/or propoxylation is carried out at about 150–170° C. in an alkaline medium.

The average degree of propoxylation or ethoxylation of these homolog mixtures corresponds to the ratio of the quantities of ethylene oxide/propylene oxide and isostearic acid monoisopropanolamide or canola fatty acid monoisopropanolamide used in the addition reaction.

The thickening agents of the present invention are compatible with almost all surface-active compounds typically used in cosmetics, hair and skin care and domestically and in industry for cleaning purposes and in the sanitary sector. The compounds can be used individually or as mixtures and are compatible with anionic, nonionic and amphoteric surfactants such as alkali metal, ammonium or magnesium alkyl sulfates or alkyl ether sulfates, secondary alkanesulfonates, alkali metal α-olefinsulfonates, sulfosuccinates, acylisethionates, sarcosides, taurides, alkylpolyglucosides, ether citrates, carboxylates, ether carboxylates, alkylamide ether sulfates and also ethoxylates of fatty alcohols, glycerides, oils, fatty acids, fatty acid esters, amine oxides, alkylbetaines, alkylamidobetaines, propionates, glycinates, acetates and sulfobetaines and sodium, potassium or triethanolamine soaps.

The viscosity-increasing agents of the present invention are generally used in amounts of from about 0.1 to about 5% by weight, preferably between 0.5 to 3.0% by weight, based on the total formulation. Their effective fraction is dependent on the nature and the amount of the particular surfactants or their mixtures used and can be optimized by means of a few simple preliminary tests in combination with the mineral salts used.

The mineral salts used in the present invention are the chlorides or sulfates of alkali or alkaline earth metals in amounts of from about 0.1 to 10% by weight, based on the total formulation. Liquid or pasty preparations may be prepared containing 0.5–4.0 parts by weight of a thickening agent based on fatty acid monoisopropanolamide, 1.0–5.0 parts by weight of a mineral salt, 10–25 parts by weight of at least one surfactant, and water to a total of 100 parts by weight.

The examples hereinbelow are carried out with a commercially available isostearic acid, which has the following average chain length distribution according to analytical values determined by gas chromatography:

C16: 12.5%
C18 iso: 70.6%
C18: 4.4%
C18': 3.4%
C18: 9.4%

The canola fatty acid used is a commercially available fatty acid which has the following average chain length distribution according to analytical values determined by gas chromatography:

C14: 1.5%
C16: 12.5%
C18: 4.5%
C18': 72.0%
C18": 9.5%

The monoisopropanolamine used is a commercially available product having a purity of 99% by weight.

The monoisopropanolamide is prepared as described in Example 1 of EP-B-0 574 277 from:

| | |
|---|---|
| Isostearic acid: | 668 g |
| Monoisopropanolamine: | 185 g |
| Phosphoric acid (85% strength) | 0.24 g |
| 2,6-Di-tert-butyl-p-cresol: (antioxidant) | 1.92 g |

Analytical data:

| | |
|---|---|
| Appearance at 20° C. | Clear liquid, tends to become cloudy in storage |
| Gardner color | 5 |
| Acid number (mg KOH/g) | 0.5 |
| % of free amine | 0.6 |
| pH, 1% strength (1:1 water/isopropanol) | 8.6 |

The reaction with ethylene oxide or propylene oxide was carried out immediately thereafter, the addition reaction taking place at 150–170° C. in an alkaline medium according to known methods.

The following examples are given to illustrate the present invention as well as to illustrate some advantages that can be obtained therefrom.

EXAMPLE 1

Addition of about 3.5 EO (ethylene oxide):

366 g of the reaction product of Example 1 of EP-B-0 574 277

154 g of ethylene oxide

Analytical data:

| | |
|---|---|
| Appearance at 20° C. | Clear liquid |
| Gardner color | 2 |
| Ester number (mg KOH/g) | 18.7 |
| Hydroxyl number (mg KOH/g) | 126.9 |

EXAMPLE 2

Addition of 2.9 EO:

366 g of the reaction product of Example 1 of EP-B-0 574 277

128 g of ethylene oxide

Analytical data:

| | |
|---|---|
| Appearance at 20° C. | Clear liquid |
| Gardner color | 2.3 |
| Ester number (mg KOH/g) | 20.1 |
| Hydroxyl number (mg KOH/g) | 137.1 |

EXAMPLE 3

Addition of 5 EO:

366 g of the reaction product of Example 1 of EP-B-0 574 277

220 g of ethylene oxide

Analytical data:

| | |
|---|---|
| Appearance at 20° C. | Clear liquid |
| Gardner color | 2 |
| Ester number (mg KOH/g) | 19.1 |
| Hydroxyl number (mg KOH/g) | 119 |

EXAMPLE 4

Addition of 1.5 PO (propylene oxide):

366 g of the reaction product of Example 1 of EP-B-0 574 277

87.1 q of propylene oxide

Analytical data:

| | |
|---|---|
| Appearance at 20° C. | Clear liquid |
| Gardner color | 3 |

EXAMPLE 5

Addition of 5 PO:

366 g of the reaction product of Example 1 of EP-B-0 574 277

290 g of propylene oxide

Analytical data:

| | |
|---|---|
| Gardner color | 2.6 |
| Ester number (mg KOH/g) | 27.7 |
| Hydroxyl number (mg KOH/g) | 122 |

EXAMPLE 6

311 g of canola fatty acid
90 g of MIPA
132 g of ethylene oxide
Analytical data:

| | |
|---|---|
| Gardner color | 2.8 |
| Acid number | 4.1 |

Application Results

Stability in Storage

At preferably normal (room temperature at about 20° C.) and low temperatures (<10° C.) of products having a varying EO/PO content, the storage stability is about 4–6 months. At higher temperatures of about 50–60° C., the storage stability is about 1 month.

Thickening Action

Illustrative recipes on the line of EP-B-0 574 277.

| | Surfactant mixture | | |
|---|---|---|---|
| viscosity test | No. 1 | No. 2 | No. 3 |
| Sodium laureth sulfate (SLES) | 10%* | 10%* | 10%* |
| Isostearic acid MIPA | 2% | — | — |
| Isostearic acid MIPA + 3.5 EO | — | 2% | — |
| Isostearic acid MIPA + 2.9 EO | — | — | 2% |
| Sodium chloride | 1–5% | 1–5% | 1–5% |
| Water | ad 100 | ad 100 | ad 100 |
| Citric acid to adjust pH to about 6.0 | | | |

*(each reckoned on solids)

Thickening action

Illustrative recipes on the line of EP-B-0 574 277.

| Viscosity test | No. 1 | No. 2 | No. 3 |
|---|---|---|---|
| Sodium laureth sulfate (SLES) | 10%* | 10%* | 10%* |
| Canola fatty acid MIPA | 2% | — | — |
| Canola fatty acid MIPA + 3.0 EO | — | 2% | — |
| Sodium chloride | 1–5% | 1–5% | 1–5% |
| Water | ad 100 | ad 100 | ad 100 |
| Citric acid to adjust pH to about 6.0 | | | |

Viscosities of test series according to Brookfield in mPa*s, at 20° C.:

| % NaCl | 1.0 | 1.5 | 2.0 | 2.5 | 3.0 | 4.0 | 4.5 |
|---|---|---|---|---|---|---|---|
| Recipe No. 1 | 92 | 1500 | 14400 | 28100 | 28100 | 7580 | 1750 |
| Recipe No. 2 | 28 | 44 | 432 | 3970 | 14400 | 31300 | 39200 |
| Recipe No. 3/SLES | — | — | 28 | — | 660 | 12500 | 28300 |

Mild Liquid Soaps

| Mild Liquid soaps having different cosurfactants | No. 1 | No. 2 |
|---|---|---|
| Sodium lauryl ether sulfate | 10%* | 10%* |
| Disodium laureth sulfosuccinate | — | 2%* |
| Sodium cocoamphoacetate | 1.5%* | 1.5%* |
| Isostearic acid MIPA** + 3 EO | ad 100 | ad 100 |
| Water | | |
| Citric acid to adjust pH to about 5.5 | | |

*(each reckoned on solids); **Monoisopropanolamide

| Brookfield viscosities at 20° C. | Recipe No. 1 | No. 2 |
|---|---|---|
| % NaCl addition | | |
| 1.5 | 28 mPas | 2000 mPas |
| 1.7 | 40 mPas | 4900 mPas |
| 3.2 | 1820 mPas | |
| 3.5 | 6350 mPas | |

Liquid Soaps with Conditioning Additive, Skin-smoothing

| | |
|---|---|
| Cocamidopropylbetaine, 45% | 10% |
| SLES 2 EO, 28% | 35% |
| Isostearic acid MIPA + 3 EO | 2.0% |
| Ricinoleamidopropyltrimonium methosulfate | 1.5% |
| Water | ad 100% |
| Citric acid to adjust pH to about 5.5 Preservative, color, perfume q.s. | |

Brookfield viscosity at 20° about 3000 mPas with about 1.5% of NaCl

Ross Miles foaming power 140/135 mm

Extremely Mild Baby Shampoo, Free of SLES

| | |
|---|---|
| Cocamidopropylbetaine, 45% | 12% |
| Disodium laureth sulfosuccinate, 40% | 20% |
| Sodium cocoamphoacetate, 40% | 5% |
| Isostearic acid MIPA + 3 EO | 2% |
| PEG-200 hydrogenated glyceryl palmate | 4% |
| Water | ad 100% |
| Citric acid to adjust pH to 5.5 | |

Brookfield viscosity 20° C.: about 5000 mPas
Ross Miles foaming power: 130/120 mm While the present invention has been particularly shown and described with respect to preferred embodiments thereof, it will be understood by those skilled in the art that the foregoing and other changes in form and detail may be made without departing from the spirit and scope of the present invention. It is therefore intended that the present invention not be limited to the exact forms and details described and illustrated, but fall within the appended claims.

What is claimed is:

1. A compound of the general formula

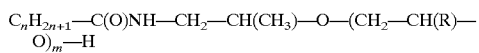

where n is from 13 to 17; R is H or $CH_3$; and m is from 1.5 to 5.5.

2. The compound of claim 1 wherein m is from 2.5 to 5.0.

3. The compound of claim 1 which is obtained by etherfying a fatty acid monoisopropanolamine with ethylene oxide or propylene oxide.

4. The compound of claim 3 wherein said fatty acid is isostearic or canola fatty acid.

5. A method of preparing a preparation comprising adding an effective amount of a compound of claim 1 to at least one surface-active agent.

6. The method of claim 5 wherein said surface-active agent is an anionic surfactant, a non-ionic surfactant or an amphoteric surfactant.

7. A preparation comprising at least 80% of a thickening agent having the formula

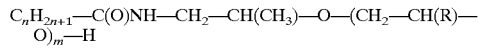

where n is from 13 to 17, R is H or $CH_3$, and m is from 1.5 to 5.5.

8. A liquid or pasty preparation comprising 0.5–4.0 parts by weight of a compound as claimed in claim 1,
  1.0–5.0 parts by weight of a mineral salt,
  10–25 parts by weight of at least one surfactant, and water to a total of 100 parts by weight.

9. The preparation of claim 8 wherein m is 2.5 to 5.0.

10. The preparation of claim 8 further comprising preservatives, perfume oils, dyes or customary auxiliary and additive substances.

11. The preparation of claim 8 wherein said surfactant is an anionic surfactant, a non-ionic surfactant or an amphoteric surfactant.

* * * * *